United States Patent [19]

von Kleinsorgen

[11] Patent Number: 4,669,492

[45] Date of Patent: Jun. 2, 1987

[54] COSMETIC STICK FOR A POWDER PENCIL

[75] Inventor: Reinhard von Kleinsorgen, Nuremberg, Fed. Rep. of Germany

[73] Assignee: Schwan-Stabilo Schwanhäusser GmbH & Co., Fed. Rep. of Germany

[21] Appl. No.: 709,305

[22] Filed: Mar. 7, 1985

[30] Foreign Application Priority Data

May 9, 1984 [DE] Fed. Rep. of Germany ....... 3417115

[51] Int. Cl.$^4$ ............................................. A45D 40/20
[52] U.S. Cl. ............................. 132/79 C; 132/79 A; 132/82 A; 132/88.5; 132/88.7; 401/49; 424/DIG. 5
[58] Field of Search ............. 401/49; 132/79 A, 79 C, 132/82 A, 88.7, 88.5; 424/63, 64, DIG. 5, 57

[56] References Cited

U.S. PATENT DOCUMENTS

| 2,941,926 | 6/1960 | Salzmann | 424/57 |
| 3,800,034 | 3/1974 | Kircher et al. | 424/63 |
| 4,264,580 | 4/1981 | Barberio | 424/57 |
| 4,332,763 | 6/1982 | Hempel et al. | 424/63 |
| 4,348,382 | 9/1982 | Pierce et al. | 424/57 |

Primary Examiner—Richard J. Apley
Assistant Examiner—Gregory Beaurage

[57] ABSTRACT

A cosmetic stick for a powder pencil comprises a stable stick body formed from powder base material and pigment, optionally with binding agent, lubricant and/or adhesion-enhancing agent, together with a particulate material which is additionally contained in the stick body in finely divided form, the particles thereof being harder than the base materials. The particulate material includes at least one derivative of tricalcium phosphate, tetracalcium phosphate or calcium pyrophosphate.

13 Claims, 5 Drawing Figures

COSMETIC STICK FOR A POWDER PENCIL

BACKGROUND OF THE INVENTION

The present invention relates generally to a cosmetic stick for forming a powder stick or pencil, for directly applying powder to the skin.

One form of cosmetic stick is disclosed in German laid open application (DE-OS) No. 31 03 128, corresponding to U.S. Ser. No. 325,493; the cosmetic stick comprises a shaped body which is formed from powder base materials and pigments, possibly with the addition of binding agent, lubricant and/or adhesion-enhancing agent. In addition to the base materials, pigments and other additives which normally go to make up a powder pencil, the above-indicated cosmetic stick also includes a particulate material which is present in finely divided form and the particles of which are harder than all the other base materials. The aim and purpose of the additional particulate material is to prevent the surface of the powder stick or pencil becoming clogged with grease or moisture when the powder pencil is rubbed against the skin to apply powder thereto. In comparison with using powder from powder compacts, which is applied by means of an applicator, applying powder by directly rubbing the surface of the powder pencil against the skin has the advantage that it is easier to do and is more hygienic. However, the fact that the surface of the powder pencil becomes clogged, which may even occur in some cases after relatively short periods of use, is found to be an extremely troublesome aspect insofar as the surface of the powder stick becomes solid and glossy or glazed as a result of such clogging by such grease and moisture, so that it no longer deposits any powder on the skin of the person using the powder pencil, hence giving rise to the necessity for fresh powder to be exposed by for example making a fresh point on the powder pencil. The above-mentioned harder particulate material effectively prevents or at least reduces such clogging.

In the known cosmetic stick, the particulate material comprises quartz flour or substances derived from silicon dioxide, for example pumice powder and it is present in a proportion of 20 to 40% by weight, with a particle size of between 10 and 100μ. In that connection, a comparatively high proportion by weight of crystalline quartz can be considered to be a disadvantage from physiological points of view; in addition, those natural substances have a comparatively wide range of particle sizes so that expensive sifting operations have to be carried out after the grinding or crushing operation, in order to produce an at least relatively uniform particle size. Finally, additional cost is involved in avoiding contamination by other substances, possibly also including heavy metals which may be present, depending on the region in which the naturally occurring raw materials were mined.

SUMMARY OF THE INVENTION

An object of the present invention is to provide an improved cosmetic stick for a powder pencil, which is more resistant to clogging by grease or moisture.

Another object of the present invention is to provide a cosmetic stick which includes particulate material which is physiologically acceptable, in a small proportion by weight.

Still another object of the present invention is to provide a cosmetic stick for a powder pencil, which is easy to produce by virtue of the nature of the materials employed therein.

A still further object of the present invention is to provide a cosmetic stick including a particulate material of at least substantially regular particle size, while being readily manufacturable.

According to the present invention, these and other objects are achieved by a cosmetic stick for a powder pencil, comprising a stable or rigid stick body which is produced for example by compacting or extruding or otherwise putting into a stable stick form, powder base material and pigment, optionally with a binding agent, a lubricant and/or an adhesion-enhancing agent, together with a particulate material which is contained in finely divided form in addition to the base materials. The particles of the particulate material are of greater hardness than the base materials. The particulate material includes one or more derivatives of tricalcium phosphate, tetracalcium phosphate or calcium pyrophosphate.

Tricalcium phosphate and the above-mentioned derivatives thereof may be produced in a narrow range of particle sizes, for example by sintering and subsequent crushing or grinding. As therefore a larger proportion of the particles in a given amount of the particulate material is of a uniform size, a larger proportion thereof is also effective in accordance with the invention in the cosmetic pencil, thereby in turn affording the possibility of a smaller amount of the additive material being used in the cosmetic stick. It has been found that the proportion by weight of particulate material in the cosmetic stick can be reduced to around 5%.

The use of derivatives of tricalcium phosphate is further based on the realisation that that material is completely acceptable and harmless from the physiological point of view and moreover can be manufactured in a narrow particle size range, without a particularly high level of technical expenditure being involved. Such derivatives, for example calcium dihydrogenphosphate, are in part already known as cleaning and polishing agents in regard to dental care.

Tricalcium phosphate or a derivative thereof is used in the cosmetic pencil, with a particle size of from 10 to 50μ. After a crushing or grinding operation, the particles have the desired irregular and rough surface.

Tricalcium phosphate or derivatives thereof may be obtained from the various naturally occurring apatite minerals which have a MOHS hardness of around 5. Those materials are ground or crushed and then subsequently sifted or sieved in order to give the particle size of from 10 to 50μ which is required for the particulate material to be used in the cosmetic stick.

However, it is also possible for the phosphate of the particulate material to be produced by sintering hydroxylapatite (formula: $Ca_5(PO_4)_3OH$), thereby achieving a further improvement in that the expenditure involved in regard to the crushing and sifting operations is reduced, while nonetheless still making it possible to produce a substantially uniform grain size.

The material which is synthetically manufactured in that way essentially comprises tricalcium phosphate. The manufacturing process generally involves operating in such a way that the hydroxyapatite, with a grain size of about 1 to 2μ resulting from the method of production thereof, is subjected to a melting and calcination process at about 1300° C., with the addition of calcium pyrophosphate (formula: $Ca_2P_2O_7$); when a molten phase occurs, depending on temperature, substantially complete conversion to tricalcium phosphate ($Ca_3(PO_4)_2$) occurs. In that connection, besides an increase in grain size, there is also a structural change in which the individual crystallites grow together to form larger bodies with a porous structure. Such bodies can be obtained by the sintering operation, with a range of grain sizes from which, by means of sifting and possibly a crushing or grinding operation before that, they can be used directly in a cosmetic stick for the purposes in question.

Particles which are produced in that fashion are particularly suitable if they have a controlled porosity of about 0.5 to 1.5$\mu$ diameter. That may be achieved by adding hydroperoxide in the sintering operation, and maintaining a suitable temperature control.

However, it is also possible to provide for reaction sintering over several hours, by admixing calcium pyrophosphate. That mode of operation produces a virtually pore-free material which can be subsequently broken up, sieved or sifted in order thereby to give the desired grain size distribution. In this respect also the expenditure is considerably lower in comparison with the process which involves dealing with natural apatite because, after the sintering operation, the phosphate is already available with a better grain size distribution.

The operation of sintering hydroxylapatite in order to produce tricalcium phosphate is known per se and described in the literature (see for example: 'Neuere Ingenieur-Technik', 47th edition 1975, No. 8; H. Heide, K. Koster, H. Lukas, 'Gesinterte Hydroxylapatit als Biokeramin'; J. G. J. Deelen, Phillips Technische Rundschau 37, No. 9/10, 255–257, 1977/78, and 'Preparation and Properties of sintered Hydroxylapatit'/Ceramurgia International, vol 4 No. 2 1978. There is therefore no need at this point to go into details in regard to manufacture thereof, the foregoing references being incorporated herein. As can be seen from the two-component system Ca/P (see E. M. Levin, C. R. Robins, H. F. MacMurdy; Phase-Diagrams for Ceramists, The American Ceramic Society (1964), FIG. 246-System CaO-$P_2O_5$; page 107), in the range of 47 to 54% by weight of calcium oxide components, it is still possible to achieve substances which can be satisfactorily melted and which thus can also be sintered and which may be compressed to form both porous bodies and also compact material.

Further objects, features and advantages of the present invention will be more clearly apparent from the following description of the invention.

DESCRIPTION OF PREFERRED EMBODIMENTS

Figure 1A:
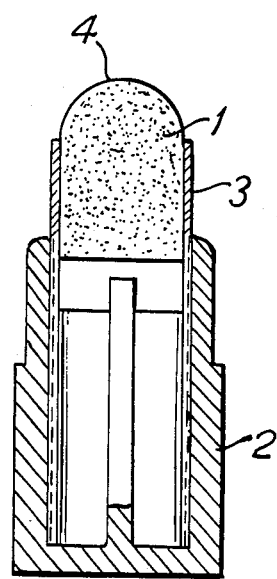
FIGS. 1a and 1b are diagrammatic views in longitudinal section of two known forms of powder pencil, incorporating a cosmetic stick constructed in accordance with the principles of this invention.

Reference will first be made to FIG. 1a showing a powder pencil which essentially comprises a cosmetic stick 1 and a container 2 which comprises metal or plastic material and in which a screw sleeve or tube 3 is accommodated. The stick 1 may be pushed out in known fashion by relative rotary movement of the screw sleeve 3 with respect to the container 2 so that the front end surface 4 of the stick 1 can be applied to the skin of the person using the powder pencil, whereby powder can be applied to the skin of that person by rubbing the stick thereover.

Figure 1B:
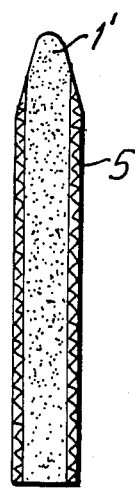

FIG. 1b shows another form of powder pencil in which the stick 1' is accommodated in a shank portion 5 comprising for example wood or plastic material which can be formed into a point in suitable fashion, so that after the tip of the stick 1' has been used up, a fresh point can be exposed thereon again by sharpening the member 5.

It will be appreciated that the external appearance of the powder pencils shown in FIGS. 1a and 1b is no different from those of known powder pencils or like cosmetic sticks. However, the makeup of the cosmetic stick 1 or 1' of the respective powder pencils is in accordance with the principles of this invention.

Figure 2:
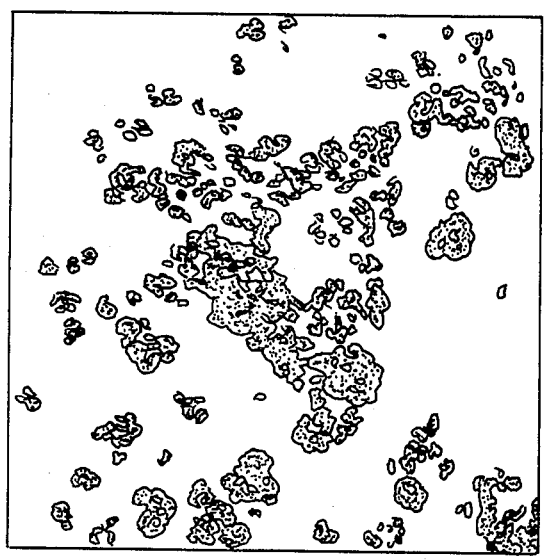
FIGS. 2 through 4 show highly enlarged representations of hydroxylapatite which is used in the cosmetic stick according to the invention, in various conditions of treatment.
Figure 3:
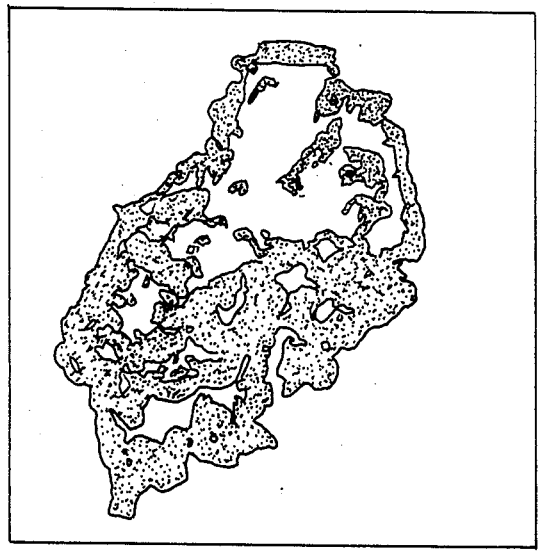
Figure 4:
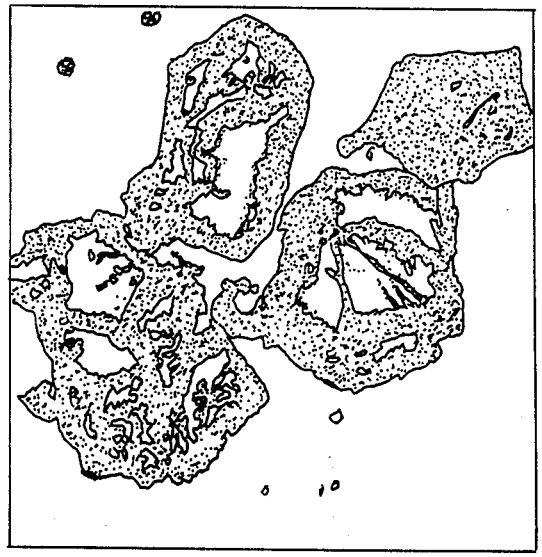

Reference will therefore now be made to accompanying FIGS. 2 through 4 are draftsman's representations showing hydroxylapatiteas an appropriate starting material prior to the sintering operation with a grain size of between 1 and 2$\mu$ (with reference to FIG. 2; insofar as particles of larger size can be seen, they are agglomerates, which are only lightly bound together, of the smaller particles). FIG. 3 shows a particle having a porous structure, which was produced by growing together of the individual crystallites in the sintering operation, while FIG. 4 shows particles as a result of the above-mentioned reaction sintering operation, which are virtually pore-free and which have been broken down to the required grain size.

Incorporating the tricalcium phosphate into the basic material for producing the cosmetic stick in accordance with the principle of this invention does not require any special process steps. In a suitable form of process, all the powder components including the tricalcium phosphate which is to be added in accordance with the invention are intimately mixed together so as to ensure that all the components are homogeneously distributed intimately with each other. After that, added to the resulting powder mix is an aqueous binding agent and the resulting kneadable material is kneaded again for the purposes of complete homogenisation thereof. The material is formed into a stable stick body by any suitable form of operation, preferably by extrusion, which is then followed by a drying operation for removing water, thereby to produce the stable stick body. The respective amounts of water added depend on the nature of the water-soluble binding agent used, these being factors of which the man skilled in the art will be aware so that there is no need for detailed consideration of those aspects herein.

In accordance with an embodiment of a cosmetic stick according to the present invention, the following substances are mixed together and processed, in accordance with the procedure outlined above:

22% by weight of talcum and 35% by weight of mica as base material (filling substances), 15% by weight of sintered hydroxylapatite which is crushed down to a particle size of from 10 to 50$\mu$ and which is of a structure as shown in FIG. 3, 4% by weight of magnesium stearate as a lubricant, 1% by weight of bentonite and 4% by weight of magnesium myristate as adhesio-enhancing agent, 2% by weight of guargum, 12% by weight of colour pigment and 5% by weight of white pigment, for example titanium dioxide.

As noted above, it has been found that it is possible for the proportion by weight of particulate material in the cosmetic stick to be reduced to about 5%, with the component of particulate material preferably being contained in the stick in a proportion of from about 5 to 40% by weight, with a further preferred proportion thereof being from about 7 to 20% by weight. Also as indicated above, the additional particulate material in accordance with this invention ensures that clogging of the surface of the cosmetic stick by grease and/or moisture from the skin when the powder of the stick is being directly applied thereto is at least substantially reduced by the stick composition according to the invention.

It will be further appreciated that the above-described embodiment of a stick in accordance with this invention is described solely by way of example thereof and that further alterations and modifications may be made therein without thereby departing from the spirit and scope of the invention.

What is claimed is:

1. A cosmetic stick for a powder pencil having a stable stick body comprising powder base material, pigment, optionally with the addition of at least one additive material selected from the group consisting of binding agent, lubricant and adhesive-enhancing agent, and a particulate material in finely divided form, which comprises particles of greater hardness than the base materials and which includes at least one material selected from the group consisting of tricalcium phosphate, tetracalcium phosphate, calcium pyrophosphate and derivatives thereof.

2. A stick as set forth in claim 1 wherein said particulate material is contained in a proportion of from substantially 5 to 40% by weight.

3. A stick as set forth in claim 2 wherein said proportion of said particulate material is from substantially 7 to 20% by weight.

4. A stick as set forth in claim 1 wherein the particle size of said particulate material is from 10 to 50$\mu$.

5. A stick as set forth in claim 1 wherein the phosphate of the particulate material is produced by sintering hydroxyl apatite ($Ca_5(PO_4)_3OH$).

6. A stick as set forth in claim 5 wherein the phosphate is sintered to form porous particles.

7. A stick as set forth in claim 6 wherein after the sintering operation said particles are from 10 to 50$\mu$ in grain size.

8. A stick as set forth in claim 6 wherein said porous particles have a pore size of from 0.5 to 1.5$\mu$ in diameter.

9. A stick as set forth in claim 5 wherein after the sintering operation the phosphate is ground to a grain size of from 10 to 50$\mu$.

10. A stick as set forth in claim 6 wherein after the sintering operation the phosphate is ground to a grain size of 10 to 50$\mu$.

11. In a powder pencil having a stick body comprising a powder base material, a pigment and a particulate material in finely divided form comprising particles which are of greater hardness than the base material, the improvement wherein said particulate material is selected from the group consisting of at least one derivative of tricalcium phosphate, tetracalcium phosphate and calcium pyrophosphate.

12. A powder pencil as set forth in claim 11 and further including at least one additive material selected from the group consisting of a binding agent, a lubricant and an adhesion-enhancing agent.

13. A powder pencil including a cosmetic stick comprising substantially the following composition: 22% by weight of talcum, 35% by weight of mica, 15% by weight of sintered hydroxyl apatite of a particle size of from 10 to 50$\mu$, 4% by weight of magnesium stearate, 1% by weight of bentonite, 4% by weight of magnesium myristate, 2% by weight of guaigum, 12% by weight of colour pigment and 5% by weight of white pigment.

* * * * *